United States Patent [19]

Samson

[11] Patent Number: 5,171,221
[45] Date of Patent: Dec. 15, 1992

[54] SINGLE LUMEN LOW PROFILE VALVED BALLOON CATHETER

[75] Inventor: Gene Samson, Milpitas, Calif.

[73] Assignee: Target Therapeutics, Fremont, Calif.

[21] Appl. No.: 650,808

[22] Filed: Feb. 5, 1991

[51] Int. Cl.$^5$ .............................................. A61M 29/00
[52] U.S. Cl. ..................................... 604/96; 604/167; 606/194
[58] Field of Search .................. 604/96, 97, 98, 99, 604/101, 246, 247, 54, 167, 158; 606/191–195

[56] References Cited

U.S. PATENT DOCUMENTS 3,402,717  9/1968  Doherty ................................ 604/99
4,654,025  3/1987  Cassou et al. ...................... 604/101
4,813,934  3/1989  Engelson et al. .................... 604/99

Primary Examiner—John D. Yasko
Attorney, Agent, or Firm—Morrison & Foerster

[57] ABSTRACT

A single lumen valved balloon catheter assembly is disclosed that consists of a single lumen catheter tube that has a distally located integral balloon and a built-in guidewire that has a distal valve member that may be moved axially to engage and block the distal end of the catheter. The diameter of the guidewire is reduced at its distal end and the diameter of the lumen of the catheter tube distally of the balloon is reduced to below that of the proximal diameter of the balloon so that the axial movement of the guidewire distally is limited.

9 Claims, 1 Drawing Sheet

SINGLE LUMEN LOW PROFILE VALVED BALLOON CATHETER

DESCRIPTION

1. Technical Field

The invention is in the general field of surgical instruments and relates specifically to a single lumen valved balloon catheter.

2. Background

Balloon catheters are used in angiography, angioplasty, and angioocclusion. They comprise a catheter that carries a distal balloon that is inflated once the target site in a vessel is reached by the distal end of the catheter. Often the vessels through which the catheter is passed are narrow and tortuous. In order for the balloon catheter to access sites in such vessels the catheter must be flexible, torqueable and of very fine diameter. To fulfill the requirements of flexibility and torqueability catheter assemblies that include a guidewire that extends through the lumen of the catheter have been developed. In operation the guidewire is advanced along a vessel pathway using wire torquing to orient the guidewire tip along the vessel. The catheter is then advanced along the guidewire with the wire held in place.

There are two general types of balloon catheters that employ guidewires: a double lumen type and a valved single lumen type. The double lumen type has concentric inner and outer lumens with the balloon being part of the outer lumen. The guidewire is extended through the inner lumen.

In the single lumen valved type, the guidewire carries a distal valve member that can be moved by axial manipulation of the guidewire to block the distal opening of the catheter. Commonly-owned U.S. Pat. No. 4,813,934 describes several embodiments of single lumen valved catheter. Designs in which the valve is located within the catheter lumen at the distal end of the balloon as well as designs in which the valve is located exteriorly of the lumen are shown in the patent. While these embodiments provided advantages over prior valved balloon catheters, they were not optimized with respect to the profile of the distal portion of the assembly, the sealing of the distal end of the catheter by the valve, or the trackability of the catheter over the guidewire.

The present invention provides a single lumen exterior located valved catheter which has improved distal portion profile, valve sealing, and trackability.

DISCLOSURE OF THE INVENTION

The present invention provides a single lumen valved balloon catheter assembly comprising in combination: (a) a single lumen catheter having a proximal end and an open distal end and an inflatable balloon segment intermediate said ends and proximate the distal end; (b) a flexible guidewire extending axially through the lumen beyond said open end, said guidewire being axially moveable within the lumen and having a proximal segment of a first diameter and a distal segment of a second diameter that is smaller than the first diameter, said first diameter being greater than the diameter of the catheter lumen distal the balloon; and (c) a flexible coil surrounding the guidewire within the balloon segment and having one of its ends fixed at one end of the balloon and its other end fixed at the other end of the balloon; and (d) a valve member carried on the guidewire beyond the open distal end of the catheter and being axially moveable by axial movement of the guidewire between a first position in which the valve member is axially spaced from the open distal end of the catheter to a second position in which the valve member is seated against and blocks the open distal end of the catheter.

BRIEF DESCRIPTION OF THE DRAWING

The drawing shows an enlarged (not to scale) sectional elevational view of an embodiment of the catheter guidewire assembly of this invention.

MODES FOR CARRYING OUT THE INVENTION

Figure 1:
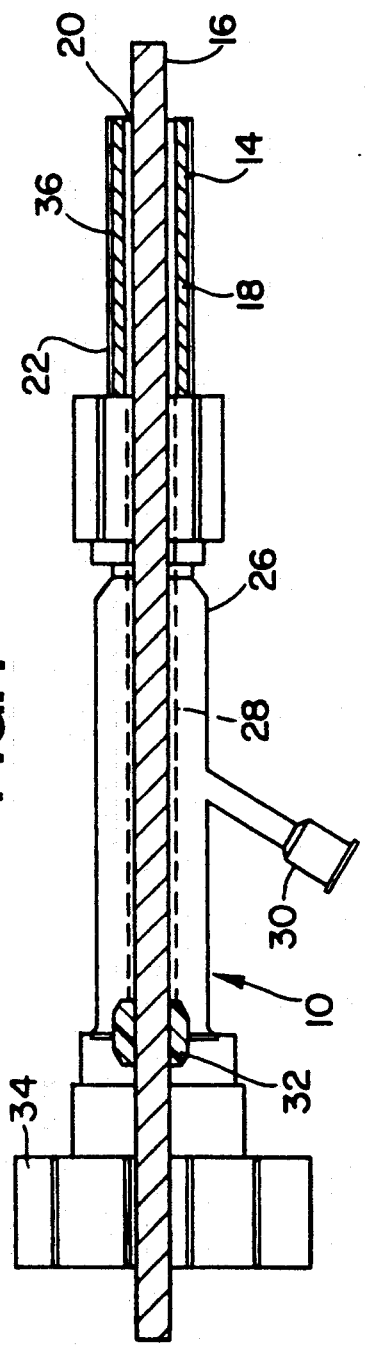
FIG. 1 depicts the proximal portion of the catheter guidewire assembly of the invention.
Figure 2:
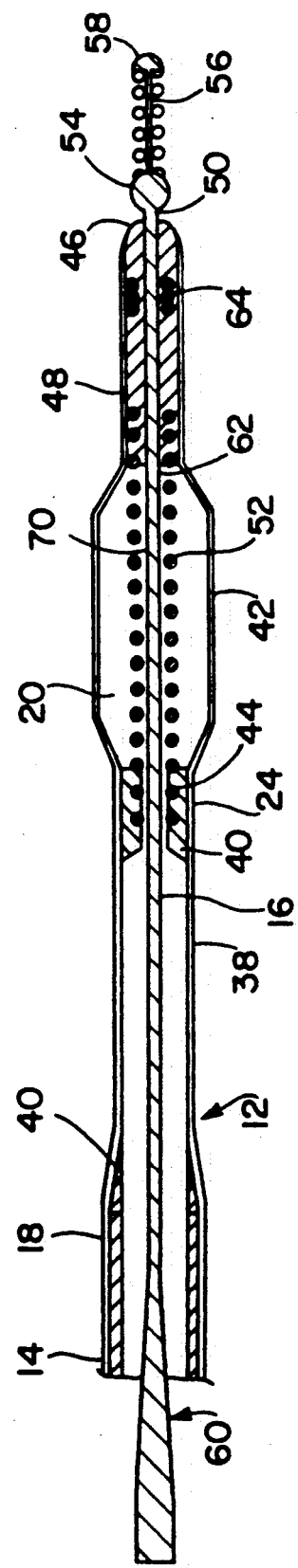
FIG. 2 depicts the distal portion of the catheter guidewire assembly of the invention.

The drawing depicts the proximal portion, generally designated 10, and distal portion, generally designated 12, of a catheter guidewire assembly constructed according to one embodiment of the invention.

The two main components of the assembly, the single lumen catheter and guidewire, are generally designated 14 and 16, respectively. The catheter is composed of a flexible thin-walled tube 18 having a single lumen 20 extending between proximal and distal end regions 22, 24, respectively. The proximal end of the catheter is received in a conventional syringe fitting 26 that has a central axial bore 28 through which the guidewire extends. The distal end of the bore communicates with the catheter lumen. The fitting is also provided with a sideport 30 that communicates with the central axial bore of the fitting. The proximal end of the central bore is fitted with a sealing ring 32. The proximal end of the guidewire carries a disc-shaped torquing handle or grip 34 for applying torque to the guidewire during the catheterization procedure.

The flexibility of the tube 18 is not uniform axially. As shown, the proximal segment 36 of tube 18 has a thicker wall and is less flexible than the distal segment 38 of the tube. The transition in wall thickness is shown at 40. It should be noted that the wall of the tube may be made of a homogeneous material or it may be formed from a layered or laminated materials. In the embodiment shown in the drawings the wall of the proximal segment is a bilayer and the wall of the distal portion is defined by an extension of only the outer layer of the proximal segment.

The wall thickness of the proximal segment of the tube will normally be 5 mil to 14 mil, more usually 10 mil to 12 mil, and preferably approximately 12 mil whereas the wall thickness of the distal segment will normally be 3 mil to 8 mil, more usually 4 mil to 6 mil, and preferably approximately 5 mil. The material(s) from which the tube is made is a medically acceptable nondistensible polymer having the appropriate mechanical properties. Preferred materials are polyethylene, polyester, polypropylene, polyimide, polyvinyl chloride.

The outer diameter of the proximal segment of the tube will normally be 33 mil to 56 mil, more usually 34 mil to 40 mil, and preferably approximately 36 mil. Correspondingly, the outer diameter of the distal segment the tube (except balloon) will normally be 28 mil to 36 mil, more usually 34 mil to 50 mil, and preferably approximately 32 mil. The diameter of the lumen of the tube (up to the balloon) will normally be 19 mil to 25 mil, more usually 20 mil to 23 mil, and preferably approximately 22 mil.

The balloon 42 of the catheter is defined by a portion of the thin-walled distal segment of the catheter tube. In its deflated configuration it has a diameter that approximates the diameter of the tube proximal to it. It will normally be inflatable to a maximum diameter with a range of sizes 1.5, 2.0, 2.5, 3.0, 3.5, 4.0 mm. There is a disc-shaped plug member 44 fixed within the lumen of the distal segment of the tube at the proximal end of the balloon. The plug has a central bore 45 through which the guidewire extends. A fixed soft plastic insert 46 is positioned within the lumen of the segment 48 of the tube that is distal to the distal end of the balloon. Its tip extends slightly beyond the tube end and is dimensioned to have as low a profile as possible for tracking over the guidewire and passing through tight vessle narrowings. This insert has a central bore 50 and serves to reduce the diameter of the distal outlet of the balloon. Typically the inner diameter of the insert (i.e., the diameter of its bore) will be 8 mil to 12 mil, more usually 9 mil to 11 mil and preferably approximately 10 mil. As shown, the guidewire extends entirely through bore 50 and out the distal end of the catheter tube.

A fixed coil 52 encloses the portion of the guidewire present in the balloon. The ends of the coil are anchored in the plug member 44 and insert 46. The inner diameter of the coil approximates the inner diameter of the insert 46. The coil is made wholly or partly of a radiopaque material, such as platinum. The coil thus serves as a means for visualizing the location of the balloon within the vessel. The coil also serves to support the balloon in its deflated state.

The guidewire carries a fixed, generally spherical valve 54 proximate its distal end. It also is wrapped with a coil 56 distally of the valve member and is terminated with a hemispherical tip 58. Further, unlike prior assemblies, the guidewire used in the present invention does not have a uniform diameter. Instead, it is composed of a proximal segment 60 and a distal segment 62 of smaller diameter than that of the proximal segment. The diameter of the proximal segment of the guidewire will usually be about 12 mil to 18 mil, more usually 14 mil, and preferably approximately 14 mil. While the transition between the larger diameter proximal segment and the smaller diameter distal segment may be a gradual taper, for ease of preparation it will typically be a step transition in which there is a defined shoulder between the two diameters. The diameter of the portion of the distal segment that extends through bore 45, the balloon, and bore 50 is such that said portion is snugly received through said bores with a small clearance that does not impede axial or torquing manipulation of the guidewire. Accordingly, the diameter of that portion will normally be 5 mil to 10 mil, more usually 7 mil to 9 mil, and preferably approximately 8 mil. The axial length of the distal segment will be at least the distance from the proximal end of restrictor 44 to the distal end of the catheter tube when the valve member 54 is seated against the tip. This length will normally be 25 cm to 50 cm, more usually 35 cm to 45 cm, and preferably 35 cm.

The smaller diameter of the distal segment provides advantages over prior valved catheter structures. The cross-sectional profile of the distal portion of the assembly may be made corresponding smaller, thus enabling access to smaller vessels. Also, the ability of the guidewire to follow tortuous vessel paths is enhanced.

The portion of the catheter tube distal to the distal end of the balloon will normally be at least about 0.5 cm or more in length, typically 0.3 to 1.5 cm and preferably about 0.7 cm. Its tip, defined by the distal end of insert 46 is soft and elastic and that it conforms to the configuration of the valve member when the valve member is pulled back against it so that the valve member is able to seat tightly against the tip. Additional radiopaque material may be incorporated closely adjacent the tip (e.g., platinum coil 64), to enable the location of the tip to be visualized when the catheter is in the vessel.

The catheter assembly of the invention is operated in a similar fashion to other valved balloon catheters. In such operation the guidewire is advanced into the desired vasculature to a desired site and the catheter tube is tracked over the guidewire. However, because of the structure of the present invention, the guidewire may be extended distally only a limited distance beyond the distal end of the catheter. That distance will be determined by the length of the reduced diameter segment of the guidewire and the length of the catheter tube that extends distally beyond the balloon. The location of the guidewire and balloon within the vessel may be determined by conventional radiology techniques. Once the balloon is at the desired site within the vessel the catheter lumen is flushed by injecting fluid through the sideport 30, the valve member is seated firmly against the distal tip of the catheter by manipulating the guidewire axially. This blocks the distal opening of the catheter tube. The balloon is then inflated by injecting fluid through the sideport 30. Since the clearance between the guidewire and the distal lumen is small, sealing is efficient. This small clearance also minimizes the possibility of aspirating blood into the balloon lumen. In addition the small sealing area reduces the likelihood of the valve and distal tip sticking together. If desired, controlled distal leakage of fluid from the catheter tip may be achieved by slight adjustment in the tightness of the seating between the valve and distal tip of the catheter. The balloon may be deflated by creating back pressure (vacuum) drawn via the sideport.

It is further noted that the guidewire is built into the assembly (i.e., it is not removable). Accordingly, no guidewire/valvewire exchanges are needed in clinical applications. Further, no time is lost in loading the guidewire and the possibility of damaging the guidewire or catheter during loading is eliminated.

The following provides an example of one procedure for manufacturing a catheter-guidewire assembly according to the invention.

A segment of radiation-hardened polyethylene tubing of known inside diameter, i.e., 0.021 inches, and known outside diameter, i.e., 0.034 inches, is heated to about 300° F. and pressurized inside a mold cavity of predetermined shape. The operation causes the heated segment to form a balloon configuration, and sections adjacent distally and proximally are also expanded to allow the insertion of the coil (52) and the hot melt polymer tubing that holds the coil in place and forms the restrictor (44) and insert 46 members. The coil can have approximate inside diameter of 0.012 inches made from a material that is fluoroscopically visible like stainless steel. The hot melt polymer tubing is positioned over the balloon coil and is heated until it has melted to hold the coil securely to the balloon tubing. This procedure is performed on both ends of the balloon segment. The segment proximal to the balloon uses a wire mandrel close to the inside diameter of the balloon coil to allow for sufficient room for adequate balloon inflation time. The segment distal to the balloon uses a wire mandrel slightly bigger than the diameter of the ground segment of the guidewire. Excess tubing material on the tip is cut so as to leave a concave-shaped tip.

The tubing is then cut to some usable length, e.g., 150 cm, and is connected to a Y-type syringe assembly, one with provision to seal the guidewire on one end of the assembly, and the other should be able to communicate with the tubing lumen on the other end. The sealing end of the Y-type assembly should be in-line with the balloon tube. The ground segment of the guidewire is then threaded through the seal port of the Y-assembly until the tip passes through the end of the balloon tube with sufficient clearance between the tip of the wire and the tip of the balloon tube. The guidewire coil is then soldered on the distal tip of the wire on both ends of the coil. The solder on the proximal end of the coil should be kept as uniformly hemispherical as possible.

The integrity of the system may be pressure tested as follows. The distal end of the balloon tube is sealed by pulling on the guidewire until intimate contact between the tip of the balloon tubing and the proximal solder on the wire is made. The balloon tubing is then pressurized up to 100 psi with air while submerging the tip in a sterile liquid for five min. to determine whether it leaks.

I claim:

1. A single lumen valved balloon catheter assembly comprising in combination:
   (a) a single lumen catheter having a proximal end and an open distal end and an inflatable balloon segment intermediate said ends and proximate the distal end;
   (b) a flexible guidewire extending axially through the lumen beyond said open end, said guidewire being axially moveable within the lumen and having a proximal segment of a first diameter and a distal segment of a second diameter that is smaller than the first diameter, said first diameter being greater than the diameter of the catheter lumen distal to the balloon; and
   (c) a flexible coil surrounding the guidewire within the balloon segment and having one of its ends fixed at one end of the balloon and its other end fixed at the other end of the balloon; and
   (d) a valve member carried on the guidewire beyond the open distal end of the catheter and being axially moveable by axial movement of the guidewire between a first position in which the valve member is axially spaced from the open distal end of the catheter to a second position in which the valve member is seated against and blocks the open distal end of the catheter.

2. The assembly of claim 1 wherein the length of said distal segment of the guidewire is at least as long as the axial distance from the proximal end of the balloon to the valve member.

3. The assembly of claim 1 wherein the clearance between the distal segment of the guidewire and the catheter lumen is of a size of permit efficient sealing and minimize the possibility of aspirating blood into the balloon lumen.

4. The assembly of claim 1 wherein the transition between the proximal and distal segments of the guidewire is a step transition.

5. The assembly of claim 1 wherein the distal tip of the catheter is made of a soft plastic that will distort and conform to the configuration of the valve member when the valve member is pressed against said distal tip.

6. The assembly of claim 5 wherein the surface of the valve member that seats against the distal tip of the catheter is generally spherical.

7. The assembly of claim 1 wherein at least a portion of the coil is made of a radiopaque material.

8. The assembly of claim 1 wherein the catheter comprises a proximal segment having a predetermined wall thickness and flexibility and a distal segment having a lesser wall thickness and more flexibility than the proximal segment.

9. The assembly of claim 1 where the diameter of the proximal segment of the guidewire is 12 mil to 18 mil and the diameter of the distal segment is 5 mil to 10 mil.

* * * * *